Figure 1:
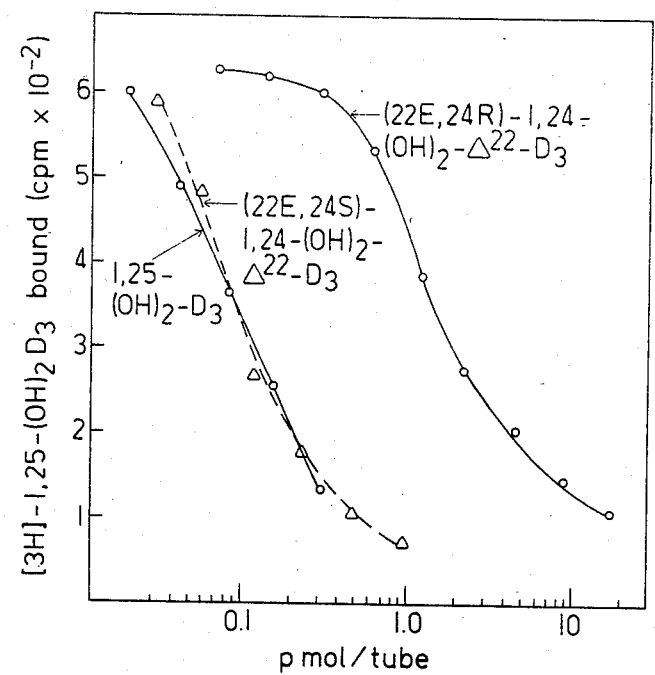

United States Patent [19]

DeLuca et al.

[11] Patent Number: 4,588,528
[45] Date of Patent: May 13, 1986

[54] 1,24-DIHYDROXY-Δ²²-VITAMIN $D_3$ AND PROCESS FOR PREPARING SAME

[75] Inventors: Hector F. DeLuca, Madison, Wis.; Nobuo Ikekawa, Tokyo, Japan; Yoko Tanaka, Madison, Wis.

[73] Assignee: Wisconsin Alumni Research Foundation, Madison, Wis.

[21] Appl. No.: 615,974

[22] Filed: May 31, 1984

[51] Int. Cl.⁴ ............................................... C07J 7/00
[52] U.S. Cl. .................... 260/397.2; 260/239.55 R; 260/239.5; 260/397.4
[58] Field of Search ................. 424/236; 260/397.2

[56] References Cited

U.S. PATENT DOCUMENTS 4,225,596 9/1980 DeLuca ........................ 260/397.2

Primary Examiner—Elbert L. Roberts
Attorney, Agent, or Firm—Howard W. Bremer

[57] ABSTRACT

The invention provides new derivatives of vitamin $D_3$ and specifically (22E,24R)-1,24-dihydroxy-Δ²²-vitamin $D_3$ and (22E,24S)-1,24-dihdroxy-Δ²²-vitamin $D_3$.

The compounds exhibit vitamin D-like activity in their ability to stimulate intestinal calcium transport, increase serum inorganic phosphorous and mineralize bone indication ready application of the compounds in the treatment of various metabolic bone diseases. The characteristic of the compounds to not mobilize bone indicates that the compositions would find ready application in combination with vitamin D and various of its derivatives to achieve controlled bone mineralization.

3 Claims, 1 Drawing Figure

1,24-DIHYDROXY-Δ²²-VITAMIN D₃ AND PROCESS FOR PREPARING SAME

This invention was made with Government support under NIH Grant No. AM-14881 awarded by the Department of Health and Human Services and NSF US/-Japan Cooperative Project R-MPC-0163 awarded by the National Science Foundation. The Government has certain rights in this invention.

DESCRIPTION

1. Technical Field

This invention relates to new derivatives of vitamin $D_3$ and to a method for their preparation.

More specifically this invention relates to 1,24-dihydroxylated-$\Delta^{22}$-vitamin $D_3$ compounds.

2. Background of the Invention

Since the discovery that the active hormonal form of vitamin D in the stimulation of intestinal calcium transport, intestinal phosphate transport, and bone calcium mobilization is 1,25-dihydroxyvitamin $D_3$ (1,25-$(OH)_2D_3$), considerable interest in the chemical synthesis of analogs of this compound has developed with a view toward finding in such analogs either increased biological activity or specific target organ actions. The most potent analogs which have been prepared to date are 26,26,26,27,27,27-hexafluoro-1,25-dihydroxyvitamin $D_3$ (26,27-$F_6$-1,25-$(OH)_2D_3$) (U.S. Pat. No. 4,358,406) and 24,24-difluoro-1,25-dihydroxyvitamin $D_3$ (24,24-$F_2$-1,25-$(OH)_2D_3$) (U.S. Pat. No. 4,201,881). These compounds provide activity at least 10 fold that of the natural hormone. All other modifications of the side-chain appear to reduce biological activity except the ergosterol side-chain which has an unsaturation at the $\Delta^{22}$-position and a methyl group in the 24S-position. This compound appears to be equally active in binding to the chick intestinal cytosol receptor and in biological activity in mammalian species, but appears to be one-tenth as active in birds. It is of interest, therefore, to construct various analogs in which each of these modifications is examined separately. Also of interest is the fact that 1,24-dihydroxyvitamin $D_3$ (1,24-$(OH)_2D_3$) is equally as active as is 1,25-$(OH)_2D_3$ in binding to the chick intestinal receptor, but when given in vivo 1,24R-$(OH)_2D_3$ is only one-tenth as active as 1,25-$(OH)_2D_3$ and that the 1,24S-isomer is even less active than the 1,24R-isomer.

DISCLOSURE OF INVENTION

Two new vitamin D derivatives have now been prepared. These compounds are the trans-isomers of 1,24-dihydroxyvitamin $D_3$ (1,24-$(OH)_2D_3$) in which a double bond has been inserted in the 22-position and an hydroxyl function substituted in the S- and R-positions on the 24-carbon atom. The compounds are respectively (22E,24S)-1,24-dihydroxy-$\Delta^{22}$-vitamin $D_3$ and (22E,24R)-1,24-dihydroxy-$\Delta^{22}$-vitamin $D_3$.

Both of the compounds exhibit vitamin D-like activity with the 24-S compound showing the greater activity of the two and approaching, in fact, the activity of 1,25-$(OH)_2D_2$.

BEST MODE FOR CARRYING OUT THE INVENTION

The compounds of this invention can be synthesized in accordance with the following schematic diagram and description in which like compounds are identified by like numbers.

In the description which follows physico-chemical measurements were determined as follows: Melting points were determined on a hot stage microscope and were uncorrected. UV spectra were obtained in ethanol solution with a Shimadzu UV-200 double beam spectrometer. $^1$H-NMR spectra were run on a Hitachi R-24A spectrometer, a JEOL PS-100 spectrometer or a JEOL FX-400 spectrometer. All NMR spectra were taken in $DCDl_3$ solution with tetramethylsilane as internal reference. Mass spectra were obtained with a Shimadzu LKB 9000S spectrometer at 70 eV. Column chromatography was effected with silica gel (Merck, 70–230 mesh). Preparative thin layer chromatography was carried out on precoated plates of silica gel (Merck, silica gel 60 $F_{254}$). The usual work-up refers to dilution with water, extraction with an organic solvent, washing to neutrality, drying over magnesium sulfate, filtration, and removal of the solvent under reduced pressure.

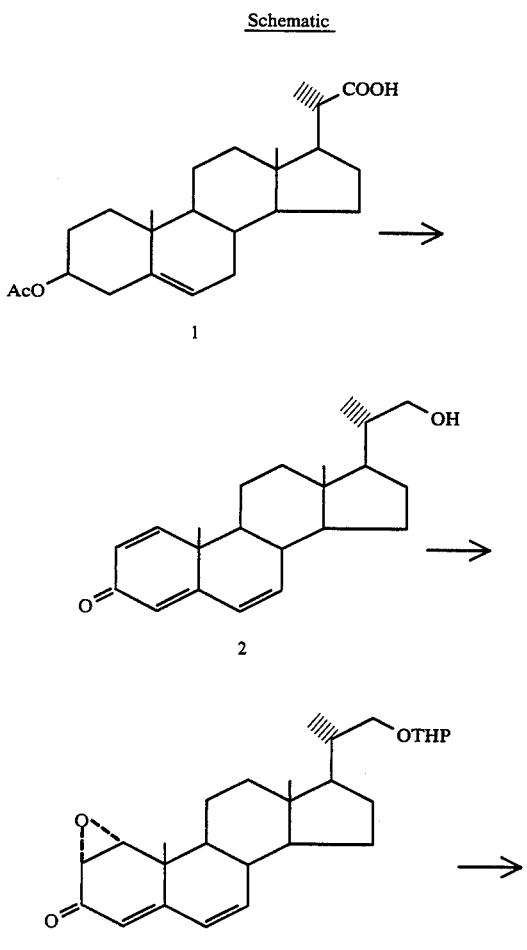

Schematic

3

-continued
Schematic

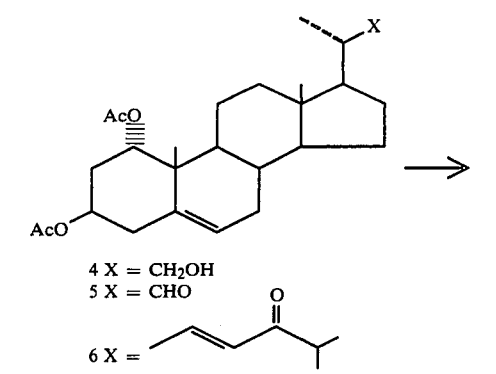

4 X = CH₂OH
5 X = CHO
6 X = <structure>

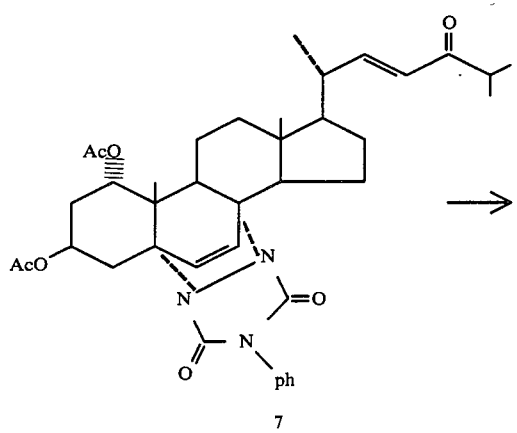

7

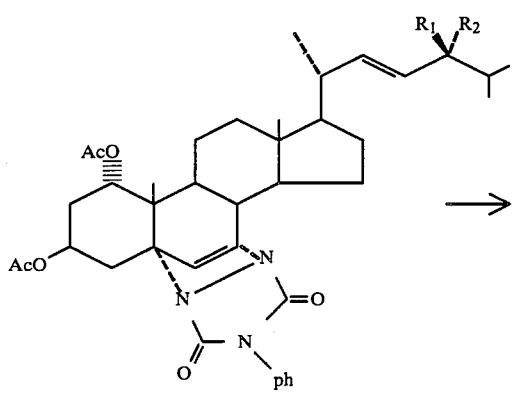

8-a R₁ = OH, R₂ = H
8-b R₁ = OMTPA, R₂ = H
9-a R₁ = H, R₂ = OH
9-b R₁ = H, R₂ = OMTPA

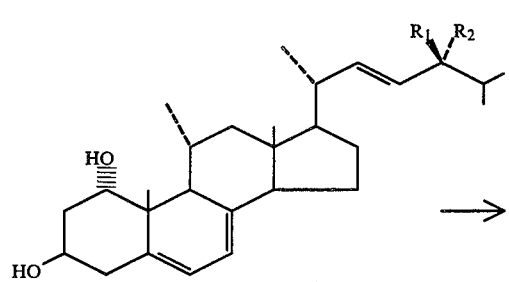

10 R₁ = H, R₂ = OH
11 R₁ = OH, R₂ = H

4

-continued
Schematic

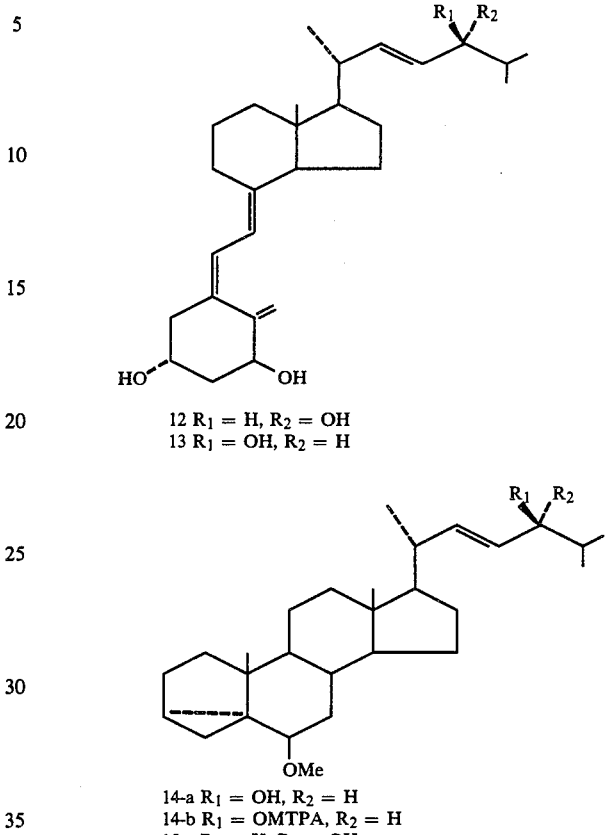

12 R₁ = H, R₂ = OH
13 R₁ = OH, R₂ = H 14-a R₁ = OH, R₂ = H
14-b R₁ = OMTPA, R₂ = H
15-a R₁ = H, R₂ = OH
15-b R₁ = H, R₂ = OMTPA

Legend:
THP = tetrahydropyranyl
MPTA — α-methoxy-α-trifluoromethylphenylacetyl
ph — phenyl

SYNTHESIS

22-Hydroxy-23,24-dinorchol-1,4,6-triene-3-one (2)

To a solution of 3β-acetoxydinorcholenic acid (1) (7.0 g, 18.04 mmole) in THF (20 mL) lithium aluminum hydride (3.0 g, 78.95 mmole) was added. This mixture was stirred at 60° C. for 14 h. To this reaction mixture water and ethyl acetate were carefully added. Filtration and removal of the solvent gave the residue (5.2 g). This in dioxane (140 mL) was treated with dichlorodicyanobenzoquinone (11.7 g, 51.54 mmole) under reflux for 14 h. After cooling to room temperature the reaction mixture was filtered and the filtrate was evaporated to leave the residue, which was applied to a column of alumina (200 g). Elution with dichloromethane provided the trienone (2) (2.8 g, 47%): mp 156°–157° (from ether). UV $\lambda_{max}^{EtOH}$ nm (ε): 299 (13000), 252 (9200), 224 (12000), ¹H-NMR (CDCl₃): 0.80 (3H, s, 18-H₃), 1.04 (3H, d, J=6 Hz, 21-H₃), 1.21 (3H, s, 19-H₃), 3.10–3.80 (3H, m, 22-H₂ and OH), 5.90–6.40 (4H, m, 2-H, 4-H, 6-H, and 7-H), 7.05 (1H, d, J=10 Hz, 1-H), MS m/z: 326 (M+), 311, 308, 293, 267, 112.

22-Tetrahydropyranyloxy-23,24-dinorchol-1α,2α-epoxy-4,6-dien-3-one (3)

The alcohol (2) (2.7 g, 8.28 mmole) in dichloromethane (50 mL) was treated with dihydropyrane (1.5 mL, 16.42 mmole) and p-toluenesulfonic acid (50 mg) at room temperature for 1 h. The usual work-up (ethyl acetate for extraction) gave a crude product. To a solution of this product in MeOH (70 mL), 30% $H_2O_2$ (4.8 mL) and 10% NaOH/MeOH (0.74 mL) were added and this mixture was stirred at room temperature for 14 h. The usual work-up (ethyl acetate for extraction) gave a crude product, which was applied to a column of silica gel (50 g). Elution with benzene-ethyl acetate (100:1) provided the epoxide (3) (1.45 g, 41%): mp 113°–115° (hexane). UV $\lambda_{max}^{EtOH}$ nm ($\epsilon$): 290 (22000), $^1$H-NMR (CDCl$_3$): 0.80 (3H, s, 18-H$_3$), 1.07 (3H, d, J=6 Hz, 21-H$_3$), 1.18 (3H, s, 19-H$_3$), 3.38 (1H, dd, J=4 and 1.5 Hz, 1-H), 3.55 (1H, d, J=4 Hz, 2-H), 3.30–4.10 (4H, m, 22-H$_2$ and THP), 4.50 (1H, m, THP), 5.58 (1H, d, J=1.5 Hz, 4-H), 6.02 (2H, s, 6-H and 7-H), MS m/z: 342 (M$^+$-DHP), 324 (M$^+$-THPOH), 309, 283, 85.

23,24-Dinorchol-5-ene-1α,3β,22-triol-1,3-diacetate (4)

Lithium (3.25 g) was added in small portions to liquid ammonia (130 mL) at −78° C. under argon atmosphere during 30 min. After stirring for 1 h at −78° C., the epoxide (3) (1.33 g, 3.12 mmole) in dry THF (100 mL) was added dropwise at −78° C. during 30 min. and this mixture was stirred for 1 h at −78° C. To this reaction mixture anhydrous NH$_4$Cl (40 g) was added in small portions at −78° C. during 1 h. After 1.5 h the cooling bath was removed and the most of ammonia was removed with bubbling argon. The usual work-up (ether for extraction) gave a crude product (1.23 g). This was treated with acetic anhydride (3 mL) and pyridine (4 mL) at room temperature for 14 h. The usual work-up (ethyl acetate for extraction) gave a crude product (1.3 g). This in methanol (4 mL) and THF (5 mL) was treated with 2 drops of 2M HCl at room temperature for 2 h. The usual work-up (ether for extraction) gave a crude product (1.1 g), which was applied to a column of silica gel (40 g). Elution with benzene-ethyl acetate (10:1) provided the 1,3-diacetate (4) (575 mg, 42%): oil, $^1$H-NMR (CDCl$_3$): 0.68 (3H, s, 18-H$_3$), 1.07 (3H, s, 19-H$_3$), 1.99 (3H, s, acetyl), 2.02 (3H, s, acetyl), 3.02–3.72 (2H, m, 22-H$_2$), 4.79 (1H, m, 3-H), 4.98 (1H, m, 1-H), 5.46 (1H, m, 6-H), MS m/z: 372 (M$^+$-CH$_3$COOH), 313, 312, 297, 279, 253.

1α,3β-Diacetoxy-23,24-dinorcholan-22-al (5)

The 22-alcohol (4) (550 mg, 1.27 mmole) in dichloromethane (20 mL) was treated with pyridinium chlorochromate (836 mg, 3.85 mmole) and sodium acetate (100 mg) at room temperature for 1 h. To this reaction mixture ether (100 mL) was added and this mixture was filtrated through a short Florisil column. The filtrate was concentrated to leave the residue, which was applied to a column of silica gel (20 g). Elution with benzene-ethyl acetate (20:1) provided the 22-aldehyde (5) (448 mg, 82%): oil, $^1$H-NMR (CDCl$_3$): 0.70 (3H, s, 18-H$_3$), 1.07 (3H, s, 19-H$_3$), 1.09 (3H, d, J=7 Hz, 21-H$_3$), 1.99 (3H, s, acetyl), 2.02 (3H, s, acetyl), 4.79 (1H, m, 3-H), 4.98 (1H, m, 1-H), 5.45 (1H, m, 6-H), 9.45 (1H, d, J=4 Hz, 22-H), MS m/z: 310 (M$^+$-2×CH$_3$COOH), 295, 253.

(22E)-1α,3β-Diacetoxy-cholesta-5,22-dien-24-one (6)

To a solution of the 22-aldehyde (5) (420 mg, 0.977 mmole) in dimethyl sulfoxide (30 mL) isobutyrylmethylenetriphenylphosphorane (2.03 g, 5.87 mmole) was added. This mixture was stirred at 95° C. for 72 h. The usual work-up (ether for extraction) gave a crude product, which was applied to a column of silica gel (10 g). Elution with benzene-ethyl acetate (10:1) provided the enone (6) (392 mg, 81%): oil, $^1$H-NMR (CDCl$_3$): 0.71 (3H, s, 18-H$_3$), 1.08 (3H, s, 19-H$_3$), 1.09 (9H, d, J=7 Hz, 21-H$_3$, 26-H$_3$, and 27-H$_3$), 1.99 (3H, s, acetyl), 2.02 (3H, s, acetyl), 4.79 (1H, m, 3-H), 4.98 (1H, m, 1-H), 5.45 (1H, m, 6-H), 5.96 (1H, d, J=16 Hz, 23-H), 6.65 (1H, dd, J=16 and 8 Hz, 22-H), MS m/z: 438 (M$^+$-CH$_3$COOH), 378 (M$^+$-2×CH$_3$COOH), 363, 335, 307, 253, 43.

(22E)-1α,3β-Diacetoxy-5α,8α-(3,5-dioxo-4-phenyl-1,2,4-triazolidino)-cholesta-6,22-dien-24-one (7)

To a solution of the enone (6) (385 mg, 0.773 mmole) in carbontetrachloride (20 mL), N-bromosuccinimide (193 mg, 1.4 eq.) was added and this mixture was refluxed for 25 min under argon atmosphere. After cooling to 0° C., the resulting precipitate was filtered off. The filtrate was concentrated below 40° C. to leave the residue. This in THF (15 mL) was treated with a catalytic amount of tetra-n-butylammonium bromide at room temperature for 50 min. Then, to this reaction mixture a solution of tetra-n-butyl-ammonium fluoride in THF (3.5 mL, 3.5 mmole) was added and this mixture was stirred at room temperature for 30 min. The usual work-up (ethyl acetate for extraction) gave a crude 5,7-diene (380 mg). This in chloroform (15 mL) was treated with a solution of 1-phenyl-1,2,4-triazoline-3,5-dione (95 mg, 0.54 mmole) in chloroform (10 mL) at room temperature for 1 h. Removal of the solvent under reduced pressure gave the residue, which was applied to a column of silica gel (10 g). Elution with benzene-ethyl acetate (5:1) provided the triazoline adduct (7) (191 mg, 37%): oil, $^1$H-NMR (CDCl$_3$): 0.83 (3H, s, 18-H$_3$), 1.01 (3H, s, 10-H$_3$), 1.08 (9H, d, J=7 Hz, 21-H$_3$, 26-H$_3$, and 27-H$_3$), 1.97 (3H, s, acetyl), 1.98 (3H, s, acetyl), 5.03 (1H, m, 1-H), 5.84 (1H, m, 3-H), 5.96 (1H, d, J=16 Hz, 23-H), 6.28 (1H, d, J=8.5 Hz, 6-H or 7-H), 6.41 (1H, d, J=8.5 Hz, 6-H or 7-H), 6.65 (1H, dd, J=16 and 8 Hz, 22-H), 7.20–7.60 (5H, m, -ph) MC m/z: 436 (M$^+$-phC$_2$N$_3$O$_2$-CH$_3$COOH), 376 (436-CH$_3$COOH), 333, 305, 251, 43.

(22E,24R)- and(22E,24S)-1α,3β-Diacetoxy-5α,8α(3,5-dioxo-4-phenyl-1,2,4-triazolidino)-cholesta-6,22-dien-24-ol (9a and 8a)

The enone (7) (150 mg, 0.224 mmole) in THF (6 mL) and methanol (6 mL) was treated with sodium borohydride (17 mg, 0.448 mmole) at room temperature for 10 min. The usual work-up (ether for extraction) gave a crude product (150 mg), which was submitted to preparative TLC (benzene-ethyl acetate, 3:1, developed seven times). The band with an Rf value 0.53 was scraped off and eluted with ethyl acetate. Removal of the solvent under reduced pressure gave the less polar (24S)-24-alcohol (8a) (43.2 mg, 28.7%): mp 142°–144° C. (ether-hexane), MS m/z: 438 (M$^+$-phC$_2$N$_3$O$_2$-CH$_3$COOH), 420, 378 (438-CH$_3$COOH), 360, 363, 345, 335, 318, 109, 43. The band with an Rf value 0.50 was scraped off and eluted with ethyl acetate to give the more polar (24R)-24-alcohol (9a) (64.8 mg, 43.1%): mp 140°–142° C. (ether-hexane). Mass spectrum of (9a) was identical with that of (8a).

(22E,24S)-1α,3β-Diacetoxy-5α,8α-(3,5-dioxo-4-phenyl-1,2,4-triazolidino)-cholesta-6,22-dien-24-ol (+)-MTPA ester (8b)

The 24 alcohol (8a) (8.3 mg, 0.0123 mmole) in pyridine (1 mL) was treated with 3 drops of (+)-MTPA-Cl at room temperature for 1 h. The usual work-up (ethyl acetate) provided the MTPA ester (8b) (10.4 mg, 95%): $^1$H-NMR (CDCl$_3$, 100 MHz): 0.85 (3H, s, 18-H$_3$), 0.88 (3H, d, 7=J Hz, 26-H$_3$), 0.92 (3H, d, J=7 Hz, 27-H$_3$), 1.04 (3H, d, J=7 Hz, 21-H$_3$), 1.08 (3H, s, 19-H$_3$), 2.03 (3H, s, acetyl), 2.06 (3H, s, acetyl), 3.27 (1H, m), 3.54 (3H, s, —OCH$_3$), 6.28 (1H, d, J=8 Hz, 6-H or 7-H), 6.41 (1H, d, J=8 Hz, 6-H or 7-H), 7.24–7.56 (5H, m, -ph).

(22E,24R)-1α,3β-Diacetoxy-5α,8α-(3,5-doxo-4-phenyl-1,2,4-triazolidino)-cholesta-6,22-dien-24-ol 24-(+)-MTPA ester (9b)

The 24-alcohol (9a) (7.9 mg, 0.0117 mmole) was converted, as described for (8b), into the MTPA ester (9b) (9.3 mg, 89%): $^1$H-NMR (CDCl$_3$, 100 MHz): 0.83 (3H, s, 18-H$_3$), 0.88 (6H, d, J=7 Hz, 26-H$_3$ and 27-H$_3$), 1.04 (3H, d, J=7 Hz; 21-H$_3$), 1.08 (3H, s, 19-H$_3$), 2.03 (3H, s, acetyl), 2.05 (3H, s, acetyl), 3.27 (1H, m), 3.54 (3H, s, —OCH$_3$), 6.28 (1H, d, J=8 Hz, 6-H or 7-H), 6.41 (1H, d, J=8 Hz, 6-H or 7-H), 7.24–7.56 (5H, m, -ph).

(22E,24S)-6β-Methoxy-3α,5-cyclo-5α-cholesta-22-en-24-ol 24-(+)-MTPA ester (14b)

The known (24S)-24-alcohol (14a) (10.1 mg, 0.0244 mmole) was converted, as described for (8b), into the (24S)-MTPA ester (14b) (8.2 mg, 54%): $^1$H-NMR (CDCl$_3$, 100 MHz): 0.72 (3H, s, 18-H$_3$), 0.89 (3H, d, J=7 Hz, 26-H$_3$), 0.93 (3H, d, J=7 Hz, 27-H$_3$), 1.02 (3H, d, J=7 Hz, 21-H$_3$), 1.04 (3H, s, 19-H$_3$), 2.75 (1H, m, 6-H), 3.33 (3H, s, —OCH$_3$), 3.54 (3H, s, —OCH$_3$.

(22E,24R)-6β-Methoxy-3α,5-cyclo-5α-cholesta-22-en-24-ol 24-(+)-MTPA ester (15b)

The known (24R)-24-alcohol (15a) (11.0 mg, 0.0266 mmole) was converted, as described for (8b), into the (24R)-MTPA ester (15b) (9.4 mg, 56%): $^1$H-NMR (CDCl$_3$, 100 MHz): 0.76 (3H, s, 18-H$_3$), 0.88 (6H, d, J=7 Hz, 26-H$_3$ and 27-H$_3$), 1.04 (3H, d, J=7 Hz, 21-H$_3$), 1.05 (3H, s, 19-H$_3$), 2.77 (1H, m, 6-H), 3.36 (3H, s, —OCH$_3$), 3.57 (3H, s, —OCH$_3$).

(22E,24R)-Cholesta-5,7,22-triene-1α,3β,24-triol (10)

The triazoline adduct (9a) (15.0 mg, 0.0223 mmole) in THF (5 mL) was treated with lithium aluminum hydride (5 mg, 0.132 mmole) under reflux for 2 h. To this reaction mixture water was added and filtered. The filtrate was concentrated under reduced pressure to leave the residue, which was submitted to preparative TLC (benzene-ethyl acetate, 1:1, developed three times). The band with an Rf value 0.35 was scraped off and eluted with ethyl acetate. Removal of the solvent provided the 5,7-diene (10) (3.3 mg, 36%), UV $\lambda_{max}^{EtOH}$: 294, 282, 272, MS m/z: 414 (M+), 396, 381, 378, 363, 353, 335, 317, 287, 269, 251, 127, 109.

(22E,24S)-Cholesta-5,7,22-triene-1α,3β,24-triol (11)

The triazoline adduct (8a) (16.5 mg, 0.0245 mmole) was converted, as described for (10), to the 5,7-diene (11) (3.5 mg, 35%). The UV and MS spectra of (11) were identical with those of (10).

(22E,24R)-1α,24-Dihydroxy-Δ$^{22}$-vitamin D$_3$ (12)

A solution of the (24R)-5,7-diene (10) (3.3 mg, 7.97 mole) in benzene (90 mL) and ethanol (40 mL) was irradiated with a medium pressure mercury lamp through a Vycor filter for 2.5 min. with ice-cooling under argon atmosphere. Then the reaction mixture was refluxed for 1 h under argon atmosphere. Removal of the solvent under reduced pressure gave a crude product, which was submitted to preparative TLC (benzene-ethyl acetate, 1:1, developed three times). The band with an Rf value 0.40 was scraped off and eluted with ethyl acetate. Removal of the solvent under reduced pressure provided the vitamin D$_3$ analogue (12) (0.59 mg, 18%). This was further purified by high performance liquid chromatography on a Zorbax-SIL column (4.6 mm×15 cm) at a flow rate of 2 ml/min with 2% methanol in dichloromethane as an eluent. The retention time of (12) was 5.2 min. UV $\lambda_{max}^{EtOH}$ 265 nm, $\lambda_{min}^{EtOH}$ 228 nm, MS m/z: 414 (M+), 396, 378, 363, 360, 345, 335, 317, 287, 269, 251, 249, 152, 135, 134, 109. $^1$H-NMR (CDCl$_3$, 400.5 MHz): 0.57 (3H, s, 18-H$_3$), 0.87, (3H, d, J=6.7 Hz, 26-H$_3$), 0.92 (3H, d, J=6.7 Hz, 27-H$_3$), 1.04 (3H, d, J=6.6 Hz, 21-H$_3$), 2.32 (1H, dd, J=13.7 and 6.6 Hz), 2.60 (1H, dd, J=13.4 and 3.4 Hz), 2.83 (1H, dd, J=12.6 and 4.0 Hz), 4.23 (1H, m, 3-H), 4.43 (1H, m, 1-H), 5.00 (1H, bs, W$_{\frac{1}{2}}$=4.3 Hz, 19-H), 5.33 (1H, bs, W$_{\frac{1}{2}}$=4.3 Hz, 19-H), 5.39 (1H, dd, J=15.2 and 7.1 Hz, 22-H), 5.51 (1H, dd, J=15.2 and 8.3 Hz, 23-H), 6.01 (1H, d, J=11.4 Hz, 6-H), 6.38 (1H, d, J=11.4 Hz, 7-H).

(22E,24S)-1α,24-Dihydroxy-Δ$^{22}$-vitamin D$_3$ (13)

The (24S)-5,7-diene (11) (3.5 mg, 8.45 mole) was transformed, as described for (12), into the vitamin D$_3$ form (13) (0.56 mg, 16%). The retention time of (13) under the above described HPLC condition was 4.7 min. The UV and MS spectra of (13) were identical with those of (12). $^1$H-NMR (CDCl$_3$, 400.5 MHz): 0.57 (3H, s, 18-H$_3$), 0.87 (3H, d, J=6.7 Hz, 26-H$_3$), 0.92 (3H, d, J=6.7 Hz, 27-H$_3$), 1.05 (3H, d, J=6.6 Hz, 21-H$_3$), 2.32 (1H, dd, J=13.7 and 6.6 Hz), 2.60 (1H, dd, J=13.4 and 3.4 Hz), 2.83 (1H, dd, J=12.6 and 4.0 Hz), 4.23 (1H, m, 3-H), 4.43 (1H, m, 1-H), 5.00 (1H, bs, W$_{\frac{1}{2}}$=4.3 Hz, 19-H), 5.33 (1H, bs, W$_{\frac{1}{2}}$=4.3 Hz, 19-H), 5.37 (1H, dd, J=15.4 and 7.5 Hz, 22-H), 5.46 (1H, dd, J=15.4 and 8.3 Hz, 23-H), 6.01 (1H, d, J=11.4 Hz, 6-H), 6.38 (1H, d, J=11.4 Hz, 7-H).

To determine the configuration at the C-24 position the 24-alcohols 8a and 9a were converted into the corresponding (+)-MPTA ester 8b and 9b. The $^1$H-NMR spectra of 8b and 9b were compared with those of the (+)-MTPA esters 14b and 15b, which were derived from the known (24S)-24-alcohol 14a and its (24R)-isomer 15a, respectively. The $^1$H-NMR data of methyl groups of 8b, 9b, 14b, and 15b are shown in Table 1.

As shown in Table 2, the $^1$H-NMR data of C-22, and C-23 protons of the (24R)-vitamin D$_3$ analog 12 and those of the known (24S)-isomer 13 were in good agreement with those of the known (24R)-allylic alcohol 15a and its (24S)-isomer 14a, respectively. These $^1$H-NMR data (as shown in Table 1 and 2) confirmed the assignment of the synthetic vitamin D$_3$ analogs 12 and 13.

TABLE 1

$^1$H—NMR (100 MHz) spectral data of methyl groups in 8b, 9b, 14b, and 15b
Chemical shift[a]

| Compound | 18-Me | 19-Me | 21-Me | 26-Me and 27-Me |
|---|---|---|---|---|
| 8b | 0.85 | 1.08 | 1.04 (J = 7) | 0.88 (J = 7), 0.92 (J = 7) |
| 9b | 0.83 | 1.08 | 1.04 (J = 7) | 0.88 (J = 7) |
| 14b | 0.72 | 1.04 | 1.02 (J = 7) | 0.89 (J = 7), 0.93 (J = 7) |
| 15b | 0.76 | 1.05 | 1.04 (J = 7) | 0.88 (J = 7) |

[a] Shifts are given in ppm and J values in Hz

TABLE 2

$^1$H—NMR spectra data of C-22 and C-23 proton in 12, 13 (400 MHz) and 14a, 15a (360 MHz)
Chemical shift[a]

| Compound | 22-H | 23-H |
|---|---|---|
| 12 | 5.39 (dd, J = 15.2, 7.1) | 5.51 (dd, J = 15.2, 8.3) |
| 15a | 5.374 (dd, J = 15.39, 6.80) | 5.494 (dd, J = 15.40, 8.23) |
| 13 | 5.37 (dd, J = 15.4, 7.5) | 5.46 (dd, J = 15.4, 8.3) |
| 14a | 5.353 (dd, J = 15.38, 7.06) | 5.448 (dd, J = 15.03, 8.20) |

[a] Shifts are given in ppm and J values in Hz

Biological Activity

The biological activity of the compounds of this invention was measured in accordance with well known procedures as indicated below.

Rats

Weanling male rats were purchased from Holtzman (Madison, WI) and fed either a low phosphorus (0.1%), high calcium (1.2%) vitamin D-deficient diet as described by Tanaka and DeLuca (Proc. Nat'l. Acad. Sci. USA (1974) 71, 1040) (Table 3) or a low calcium (0.02%), adequate phosphorus (0.3%) vitamin D-deficient diet as described by Suda et al (J. Nutrition (1970) 100, 1049) (Table 4) for 3 weeks.

Determination of Serum Calcium and Inorganic Phosphorus

Serum calcium was determined by atomic absorption spectrometry using samples diluted in 0.1% lanthanum chloride. The instrument used was a Perkin-Elmer atomic absorption spectrometer model 403. Serum inorganic phosphorus was determined by the method of Chen et al (Anal. Chem. (1956) 28, 1756).

Measurement of Bone Ash

Bone ash measurements were made on femurs. Connective tissue was removed, the femurs extracted successively for 24 h with 100% ethanol followed by 24 h with 100% diethyl ether using a Soxhlet extractor. The fat-free bone was dried 24 h and ashed in a muffle furnace at 650° for 24 H.

Measurement of Intestinal Calcium Transport Activity

Intestinal calcium transport was measured using the everted duodenal sac method described by Martin and DeLuca (Am. J. Physiol. (1969) 216, 1351).

Displacement of 1,25-(OH)$_2$—[26,27-$^3$H]D$_3$ from Chick Intestinal Cytosol Receptor Protein by Either Compound Displacement of 1,25-(OH)$_2$-[26,27-$^3$H]D$_3$ from chick intestinal receptor was determined according to the method of Shepard et al (Biochem. J. (1979) 182, 55-69).

The results obtained in these measurements are shown in FIG. 1 and in Tables 3 and 4.

TABLE 3

Increase of serum inorganic phosphorus concentration and bone ash in response to either (22E,24R)-1,24-(OH)$_2$—$\Delta^{22}$D$_3$, (22E,24S)-1,24-(OH)$_2$—$\Delta^{22}$-D$_3$ or 1,25-(OH)$_2$D$_3$.

| compound given | serum inorganic phosphorus (mg/100 ml) | bone ash (mg) |
|---|---|---|
| None | 2.4 ± 0.1*[a] | 35.0 ± 4.6[e] |
| 1,25-(OH)$_2$D$_3$ | 3.3 ± 0.4[b] | 53.2 ± 6.9[f] |
| (22E,24R)-1,24-(OH)$_2$—$\Delta^{22}$-D$_3$ | 2.7 ± 0.4[c] | 35.0 ± 6.7 |
| (22E,24S)-1,24-(OH)$_2$—$\Delta^{22}$-D$_3$ | 2.9 ± 0.4[d] | 46.5 ± 4.2[g] |

Weanling male rats were fed a rachitogenic diet for 3 weeks. They were then given 32.5 p mol/day of either compound dissolved in a 0.1 ml mixture of 95% ethanol/propylene glycol (5/95) subcutaneously daily for 7 days. Rats in a control group were given the vehicle. Each group had 6–7, rats.
*Standard deviation of the mean.
Significantly different:
[a] from [b] $p<0.001$
[c] $p<0.025$
[d] $p<0.005$
[e] from [f] & [g] $p<0.001$
[f] from [g] $p<0.05$

TABLE 4

Increase of intestinal calcium transport and serum calcium concentration in response to either (22E,24R)-1,24-(OH)$_2$—$\Delta^{22}$-D$_3$, (22E,24S)-1,24-(OH)$_2$—(OH)$_2$—$\Delta^{22}$-D$_3$ or 1,25-(OH)$_2$D$_3$.

| compound given | intestinal calcium transport (Ca serosal/Ca mucosal) | serum calcium (mg/100 ml) |
|---|---|---|
| none | 2.5 ± 0.3*[a] | 3.5 ± 0.1[e] |
| 1,25-(OH)$_2$D$_3$ | 6.4 ± 1.1[b] | 3.8 ± 0.1[f] |
| (22E,24R)-1,24-(OH)$_2$—$\Delta^{22}$-D$_3$ | 3.4 ± 0.6[c] | 3.4 ± 0.1 |
| (22E,24S)-1,24-(OH)$_2$—$\Delta^{22}$D$_3$ | 3.9 ± 0.4[d] | 3.6 ± 0.1 |

Weanling male rats were fed a low calcium-vitamin D deficient diet for 3 weeks. They were then given 32.5 p mol/day of either compound dissolved in a 0.1 ml mixture of 95% ethanol/propylene glycol (5/95) subcutaneously daily for 7 days. Rats in a control group received the vehicle. Each group had 7 rats.
*Standard deviation of the mean.
Significantly different:
[a] from [b] & [d] $p<0.001$
[a] from [c] $p<0.005$
[b] from [c] & (d) $p<0.001$
[e] from [f] $p<0.005$ FIG. 1 demonstrates the ability of the two synthetic 1,24-(OH)$_2$D$_3$ isomers to displace radiolabeled 1,25-(OH)$_2$D$_3$ from the chick intestinal receptor. The results demonstrate that the 24S-isomer is equally potent as unlabeled 1,25-(OH)$_2$D$_3$ in displacing radiolabeled 1,25-(OH)$_2$D$_3$ from the receptor. The 24R-isomer proved to be approximately one-tenth as active as either 1,25-(OH)$_2$D$_3$ or the S-isomer. In the stimulation of intestinal calcium transport of rats on a low calcium vitamin D-deficient diet, it is apparent that neither isomer equalled 1,25-(OH)$_2$D$_3$ in this capacity (Table 4). This contrasts with the results obtained with the chick intestinal receptor in which the S-isomer equalled 1,25-(OH)$_2$D$_3$ in its ability to displace radiolabeled 1,25-(OH)$_2$D$_3$ from the receptor. Neither isomer at the doses administered was able to elicit a bone calcium mobilization response as revealed by elevation of serum calcium of rats on a low calcium diet. In contrast, 1,24-(OH)$_2$D$_3$ did stimulate this response to a minimal degree at this dosage.

Table 3 illustrates the ability of the isomers to mineralize femur of rachitic rats. The dosage used 1,25-

$(OH)_2D_3$ was fully able to mineralize rachitic femur within 7 days. On the other hand, the R-isomer was unable to mineralize significant amounts of bone at this dosage level, whereas the 24S-compound was less active than $1,25-(OH)_2D_3$ but was clearly effective in this capacity.

The rise in serum inorganic phosphorus concentration in animals on a low phosphorus diet is a critical response for mineralization of bone. It is evident that all three forms of vitamin D stimulated serum inorganic phosphorus levels; however, neither isomer was equal to $1,25-(OH)_2D_3$ in this capacity.

The measured biological activity of the compounds of this invention point to their use in physiological situations where vitamin D-like activity is indicated. The 1,24S-isomer can, in fact, be regarded as a very potent 1-hydroxylated form of vitamin D that would find application where preferential effectiveness on intestine and bone mineralization, as opposed to bone mobilization, would appear to be in order.

The compounds of this invention, or combinations thereof with other vitamin D derivatives or other therapeutic agents, can be readily administered as sterile parenteral solutions by injection or intravenously, or by alimentary canal in the form of oral dosages, or transdermally, or by suppository. Doses of from about 0.5 micrograms to about 25 micrograms per day of the compounds, per se, or in combination with other vitamin D derivatives, the proportions of each of the compounds in the combination being dependent upon the particular disease state being addressed and the degree of bone mineralization and/or bone mobilization desired, are generally effective to practice the present invention. Although the actual amount of the compounds used is not critical, in all cases sufficient of the compound should be used to induce bone mineralization. Amounts in excess of about 25 micrograms per day of the compounds, alone, or in combination with a bone mobilization-inducing vitamin D derivative, are generally unnecessary to achieve the desired results and may not be economically sound practice. In practice the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

Dosage forms of the compounds can be prepared by combining them with non-toxic pharmaceutically acceptable carriers as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, troches or lozenges. If a liquid carrier is used, soft gelatin capsules, or syrup or liquid suspension, emulsions or solutions may be the dosage form. The dosage forms may also contain adjuvants, such as preserving, stabilizing, wetting or emulsifying agents, solution promoters, etc. They may also contain other therapeutically valuable substances.

It is to be understood that the acylated derivatives of compounds 10, 11, 12 and 13 are also to be considered within the scope of the present invention, certain acylates being susceptible to administration as described for compounds 12 and 13, with conversion of the acylates to the hydroxy derivatives being accomplished in vivo. Thus, the compounds have the structures

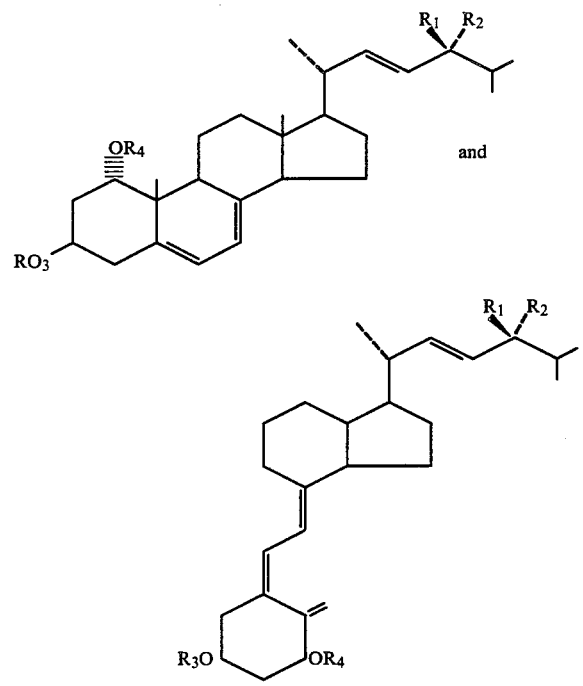

wherein
$R_1$ and $R_2$ are hydrogen or hydroxy except that when $R_1$ is hydrogen $R_2$ is hydroxy and when $R_1$ is hydroxy $R_2$ is hydrogen and
$R_3$ and $R_4$ are each hydrogen or acyl having from 1 to 4 carbon atoms.

Also, if desired, the compounds of this invention may be obtained in crystalline form by dissolution in a suitable solvent or solvent system, e.g. methanol-ether, methanol-hexane and then removing the solvent(s) by evaporation or other means as is well known.

We claim:
1. Compounds having the formula

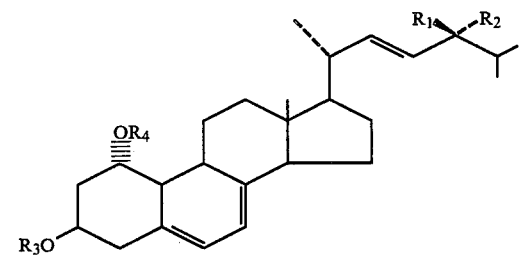

wherein
$R_1$ and $R_2$ are hydrogen or hydroxyl except that when $R_1$ is hydrogen $R_2$ is hydroxyl and when $R_1$ is hydroxyl $R_2$ is hydrogen; and
$R_3$ and $R_4$ are hydrogen or acyl having from 1 to 4 carbon atoms.
2. (22E,24R)-cholesta-5,7,22-triene-1α,3β,24-triol.
3. (22E,24S)-cholesta-5,7,22-triene-1α,3β,24-triol.

* * * * *